United States Patent [19]

Damani

[11] Patent Number: 5,198,220

[45] Date of Patent: Mar. 30, 1993

[54] SUSTAINED RELEASE COMPOSITIONS FOR TREATING PERIODONTAL DISEASE

[75] Inventor: Nalinkant C. Damani, Cincinnati, Ohio

[73] Assignee: The Procter & Gamble Company, Cincinnati, Ohio

[21] Appl. No.: 573,604

[22] Filed: Aug. 24, 1990

Related U.S. Application Data

[63] Continuation-in-part of Ser. No. 439,066, Nov. 17, 1989, abandoned.

[51] Int. Cl.⁵ .................. A61K 47/22; A61K 47/34
[52] U.S. Cl. ................................ 424/426; 424/486; 514/772.6
[58] Field of Search ............... 424/434, 435, 426, 486; 514/772.6

[56] References Cited

U.S. PATENT DOCUMENTS

| | | | |
|---|---|---|---|
| 3,736,646 | 6/1973 | Schmitt et al. | 29/458 |
| 3,867,190 | 2/1975 | Schmitt et al. | 117/138.8 |
| 4,017,615 | 4/1977 | Shastu et al. | 424/241 |
| 4,328,204 | 5/1982 | Wasserman et al. | 424/19 |
| 4,443,430 | 4/1984 | Mattei et al. | 424/78 |
| 4,454,110 | 6/1984 | Caslavsk et al. | 424/54 |
| 4,568,536 | 2/1986 | Kronenthal et al. | 424/22 |
| 4,624,256 | 11/1986 | Messier et al. | 128/335.5 |
| 4,650,665 | 3/1987 | Kronenthal et al. | 424/435 |
| 4,652,441 | 3/1987 | Okada et al. | 424/19 |
| 4,670,252 | 6/1987 | Sampathkumar | 424/53 |
| 4,685,883 | 8/1987 | Jernbrg | 433/215 |
| 4,711,782 | 12/1987 | Okada et al. | 424/455 |
| 4,713,243 | 12/1987 | Sheraldi et al. | 424/151 |
| 4,810,775 | 3/1989 | Bendix et al. | 528/480 |

FOREIGN PATENT DOCUMENTS

| | | |
|---|---|---|
| 0140766 | 5/1985 | European Pat. Off. |
| 0241178 | 10/1987 | European Pat. Off. |
| 0297535 | 1/1989 | European Pat. Off. |
| 63-79817 | 4/1988 | Japan |
| 63-287719 | 11/1988 | Japan |

*Primary Examiner*—Thurman K. Page
*Attorney, Agent, or Firm*—Douglas C. Mohl; Kim William Zerby; Jack D. Schaeffer

[57] ABSTRACT

This invention relates to compositions/devices and methods for treating diseases of the oral cavity in humans and lower animals using polylactide/glycolide compositions/devices for releasing drugs in the oral cavity.

7 Claims, No Drawings

SUSTAINED RELEASE COMPOSITIONS FOR TREATING PERIODONTAL DISEASE

CROSS REFERENCE TO RELATED APPLICATION

This is a continuation-in-part application of application Ser. No. 439,066, filed Nov. 17, 1989 and now abandoned.

TECHNICAL FIELD

This invention relates to compositions/devices for treating diseases of the oral cavity which compositions/devices are placed in or around the periodontal pocket. The invention also relates to methods of using the compositions/devices in humans and lower animals suffering from such diseases.

Periodontal disease, for example, is a major cause of tooth loss in adults. Tooth loss from periodontal disease is a significant problem beginning at age 35, but even by age 15 it is estimated that about 4 out of 5 persons already have gingivitis and 4 out of 10 have periodontitis.

While good oral hygiene, as achieved by brushing the teeth with a cleansing dentifrice, may help reduce the incidence of periodontal disease, it does not necessarily prevent or eliminate its occurrence. This is because microorganisms contribute to both the initiation and progress of periodontal disease. Thus, in order to prevent or treat periodontal disease, these microorganisms must be suppressed by some means other than simple mechanical scrubbing. Towards this end, there has been a great deal of research aimed at developing therapeutic dentifrices, mouthwashes, and methods of treating periodontal disease which are effective in suppressing these microorganisms.

Recent developments in the art are directed toward delivering the therapeutic agent directly to the periodontal pocket, in some cases in a controlled release formulation. Gordon et al. have described the use of a drug-filled polymer hollow fiber. (J. M. Goodson et al., "Periodontal Therapy by Local Delivery of Tetracyclineine", *J. Clin. Periodontal.* 6, 83 (1979), J. Lindhe et al., "Local Tetracycline Delivery Using Hollow Fiber Devices in Periodontal Therapy", *J. Clin. Periodontal.* 6, 141 (1979) and R. L. Dunn et al., "Monolithic Fibers for Controlled Delivery of Tetracycline", in *Proc. Ninth Int. Symposium on Controlled Release of Bioactive Materials.* Ft. Lauderdale, Fla., July (1982). This device is tied around a tooth and gently pressed below the margin of the gingiva so that it resides in the periodontal pocket, and is capable of delivering an effective dose of 2.5 micrograms of tetracycline per day per periodontal pocket for a prolonged period of a week or more. Similar results have been obtained by Coventry and Newman (J. Coventry and H. N. Newman, "Experimental Use of a Slow Release Device Employing Chlorhexidine Gluconate in Areas of Acute Periodontal Inflammation", *J. Clin. Periodontal.* 9, 129 (1982) and Addy et al. (M. Addy et al., "The Development and in vitro Evaluation of Acrylic Strips and Dialysis Tubing for Local Drug Delivery", *J. Periodontal* 53, 693 (1982) using acrylic strips 1 mm or more long, impregnated with chlorhexidine, tetracycline or metronidazole, which were inserted into the periodontal pocket with tweezers. Such a strip, formed from ethylcellulose impregnated with metronidazole, is disclosed by Loesche in U.S. Pat. No. 4,568,538 (February 1986). Another strip, employing a water soluble polymer of a particular elasticity and viscosity, is disclosed by Suzuki et al. in U.S. Pat. No. 4,569,837.

In addition to the above approaches, the prior art also discloses using putty-like compositions containing an antimicrobial for insertion into the periodontal pocket. A material disclosed as suitable is a copolymer of lactide and glycolide. See U.S. Pat. No. 4,650,665, Mar. 17, 1987 to Kronenthal et al., incorporated herein by reference.

The present inventor has discovered that lactide and glycolide copolymers have limited pliability and solubility in terms of processing.

It is therefore an object of the present invention to provide lactide/glycolide compositions/devices suitable for treating diseases of the oral cavity overcoming such problems.

It is a further object of the present invention to provide such compositions/devices using copolymers of lactide and glycolide and using propylene carbonate as a solvent/plasticizer.

It is still a further object of the present invention to provide a method of treating periodontal disease.

All percentages and ratios used in here are by weight unless otherwise indicated.

All measurements are made at 25° C. unless otherwise indicated.

SUMMARY OF INVENTION

The present invention relates to compositions/devices and methods for treating diseases of the oral cavity by inserting the compositions/devices into the periodontal pocket or around said pocket of humans and/or lower animals. The compositions/devices comprise copolymers of lactide and glycolide, propylene carbonate as a solvent/plasticizer and an agent providing relief of oral cavity diseases.

DETAILED DESCRIPTION OF THE INVENTION

The essential as well as optional components of the compositions/devices of this invention are described below.

Lactide/Glycolide Copolymers

The copolymers of the present invention contain mixtures of lactide and glycolide monomers. Lactide monomeric species preferably comprise 15% to about 85%, most preferably from about 35% to about 65%, of the polymers while glycolide monomers comprise from about 15% to about 85% of the polymer, preferably from about 35% to about 65% on a molar basis. The molecular weight of the copolymer lies in the range of from about 1000 to about 120,000 (number average). These polymers are described in detail in U.S. Pat. No. 4,443,430, Apr. 17, 1984, to Mattei incorporated herein by reference.

The polymer generally comprises from about 10% to about 90%, preferably from about 20% to about 70% of the compositions/devices of the present invention. Less polymer is necessary as the amount of lactide goes up.

Propylene Carbonate

The second essential component of the present invention is propylene carbonate. This is a material of commerce and is used in the present compositions/devices at a level of from about 0.1% to about 90%, preferably from about 1% to about 70%, most preferably from about 3% to about 50%. The higher levels of propylene carbonate, such as from about 25% to about 90%, are used when it is desired that the compositions be in gel or liquid form rather than in solid form.

Drug Active

The drugs useful for use in the present compositions/devices are varied and many and include any agent which provides treatment or prevention management of diseases of the oral cavity. Some therapeutic agents which are amenable to delivery by this means and are potentially of value for periodontal therapy, include (but are not limited to) antibacterial agents such as iodine, sulfonamides, mercurials, bisbiguanides, or phenolics; antibiotics such as tetracycline, neomycin, kanamycin, metronidazole, or clindamycin; antiinflammatory agents such as aspirin, naproxen, ibuprofen, flurbiprofen, indomethacin, eugenol, or hydrocortisone; immune-suppressive or stimulatory agents such as methotrexate or levamasole; dentinal desensitizing agents such as strontium chloride or sodium fluoride; odor masking agents such as peppermint oil or chlorphyll; immune reagents such as immunoglobulin or antigens; local anesthetic agents such as lidocaine or benzocaine; nutritional agents such as amino acids, essential fats, and vitamin C; antioxidants such as alphatocopherol and butylated hydroxy toluene; lipopolysaccharide complexing agents such as polymyxin; or peroxides such as urea peroxide. It is recognized that in certain forms of therapy, combinations of these agents in the same delivery system may be useful in order to obtain an optimal effect. Thus, for example, an antibacterial and an antiinflammatory agent may be combined in a single delivery system to provide combined effectiveness.

The drug active is used at a level of from about 1% to about 90%, preferably from about 5% to about 75%, most preferably from about 10% to about 50% of the compositions/devices. The compositions/devices, for example, are designed to release drug to provide steady state number average concentrations of from about 10 μg to about 2000 μg, preferably from about 50 μg to about 1500 μg, most preferably from about 100 μg to about 1000 μg per milliliter of the gingival crevicular fluid of a treated periodontal pocket. The steady state release rates can be altered by varying component ratios of the compositions. The steady state conditions are preferably used since initial bursts are accounted for as well as delays in release. For example, in the case of a ten (10) day therapy, steady state is generally reached in about one to two days.

Optional Components

In addition to the drug active, the compositions/devices of the present invention may include a variety of optional components. Such components include, but are not limited to, surfactants, viscosity controlling agents, complexing agents, antioxidants, other polymers such as carboxymethyl cellulose, gums such as guar gum, waxes/oils such as castor wax, castor oil, glycerol, dibutyl phthalate and di(2-ethylhexyl) phthalate as well as many others. If used, these optional components comprise from about 0.1% to about 20%, preferably from about 0.5% to about 5% of the total composition/device.

METHOD OF MANUFACTURE

Method of manufacturing the compositions/devices of this invention are disclosed in the Examples.

The following Examples further describe and demonstrate the preferred embodiments within the scope of the present invention. The Examples are given solely for the purpose of illustration and are not to be construed as limitations of the present invention as many variations thereof are possible without departing from its spirit and scope.

EXAMPLE I

The following is an exemplary composition/device of the present invention.

|  | Wt. % |
| --- | --- |
| Tetracycline hydrochloride | 50 |
| Poly(lactyl-co-glycolide)/50:50 copolymer | 45.4 |
| Propylene Carbonate | 4.6 |

The above composition can be prepared in a number of different ways. One way is as follows: Polymer is charged into a 110° C., electrically heated mixer, equipped with high shear Sigma type rotor blades. Propylene carbonate is added and mixed into the polymer. The drug is added and mixed until uniform. The drug polymer blend is removed for further processing into desired size and shape devices.

The compositions/devices of the invention of this application are inserted into the periodontal pocket or gingival region, and may be administered in the form of a particle, film or sheet. The size, shape, and thickness can be changed according to the condition of the disease to be treated and they are not particularly critical. Ordinarily, the size, shape, and thickness are changed according to the size of the periodontal pocket of the patient or the condition of the gingiva. The devices may be for example of a size such that the thickness is in the range of 0.01 to 2 mm, preferably from about 0.1 to about 1 mm; the width in the range of 0.1 to about 5 mm, preferably from about 0.1 to about 4 mm; and the length in the range of from about 1 to about 15 mm, preferably from about 3 to about 10 mm.

If in the above example, the propylene carbonate level is increased to about 30%, the composition is in the form of a gel which may be put into the periodontal pocket.

EXAMPLE II

Given below is another composition/device of the present invention:

|  | Wt. % |
| --- | --- |
| Chlorhexidine acetate | 10 |
| Poly(lactide-co-glycolide) 65:35 copolymer | 75 |
| Guar Gum | 9 |
| Propylene Glycol | 14 |

EXAMPLE III

Given below is still another composition/device representative of the present invention:

|  | Wt. % |
|---|---|
| Clindamycin phosphate | 20 |
| Poly(lactide-co-glycolide) 50:50 copolymer | 60 |
| Carboxymethyl cellulose sodium | 15 |
| Triacetin | 5 |

EXAMPLE IV

|  | Wt. % |
|---|---|
| Tetracycline hydrochloride | 50 |
| Poly(lactyl-co-glycolide)/50:50 copolymer | 45.4 |
| Propylene Carbonate | 4.6 |

The composition of the Example IV was tested in human volunteers having periodontal disease. For the purpose of this test, periodontally involved sites were selected in five periodontitus human volunteers. Strips of the composition of Example IV, having about 0.75 mm thickness and about 0.9 mm width were cut in length to fit individual pocket depth in length, and inserted into the cavities. Samples of gingival crevicular fluid from each of the treated sites were collected daily for at least 10 days using Periopaper ®. Volume of the collected fluid was determined using Periotron ® instrument, model number 6000. All the samples were analyzed for the drug content using microbiological bioassay procedure. Results of this test are shown in the following:

|  |  | Micrograms Drug in Gingival Crevicular Fluid |  |  |  |  |  |  |  |  |
|---|---|---|---|---|---|---|---|---|---|---|
| Subject |  |  |  |  |  |  |  |  |  |  |
| ID | Day # |  |  |  |  |  |  |  |  |  |
| RT |  | 1619 | 475 | 3366 | 710 | 463 | 613 | 558 | 2734 | 947 | 1104 |
| PA |  | 1413 | 504 | 162 | n/a | 742 | 1559 | 1780 | 385 | 1780 | 160 |
| FL |  | 24 | 34 | 56 | 76 | 180 | 2654 | 794 | 162 | 860 | 63 |
| GP |  | 70 | 87 | 578 | 1262 | 431 | n/a | 43 | 831 | 1471 | n/a |
| CB |  | 1516 | 1329 | n/a | n/a | 1625 | 905 | 774 | 1777 | 3466 | 1492 |

The devices were removed by flushing from the treated sites on the 12th day following their insertion.

The above results show that the drug is released in a sustained manner for over a week, which is adequate for the antibiotic treatment of periodontally involved sites.

While solid phase devices of the compositions illustrated above are very useful and convenient for most treatments, there may also be need for fluid compositions that can be inserted via syringe, and either a needle or catheter into the periodontal cavities. Examples of such instances include difficult to reach areas where the periodontal cavities are irregular, narrow and very deep or those involving furcations. For this reason, fluid gel or paste compositions are developed based on the above mentioned principles of the compounding the poly(lactyl-co-glycolide) polymers as illustrated in the following:

Laboratory studies have been conducted for gel compositions using propylene carbonate as carrier solvent with or without propylene and/or polyethylene glycol for poly(lactyl-co-glycolide) polymer. Representative examples of such sustained release compositions are as follows:

|  | Wt. % |
|---|---|
| EXAMPLE V |  |
| Tetracycline hydrochloride | 27 |
| Poly(lactyl-co-glycolide) | 24 |
| Propylene carbonate | 44 |
| EXAMPLE VI |  |
| Tetracycline Base | 27 |
| Poly(lactyl-co-glycolide) | 24 |
| Propylene carbonate | 40 |
| Polyethylene glycol 400 | 9 |
| EXAMPLE VII |  |
| Chlorhexidine diacetate | 40 |
| Poly(lactyl-co-glycolide)/50:50 copolymer | 20 |
| Propylene carbonate | 40 |

Compositions corresponding to the above Examples can be prepared by a variety of pharmaceutical or cosmetic procedures. For example, composition of Example IV can be prepared by first dissolving the copolymer into the propylene carbonate using a propeller mixer. Micronized drug is slowly added and mixed into the polymeric solution to a uniform consistency. Such compositions are gel like fluids which can be inserted into the diseased periodontal cavities via syringe.

Surprising feature of such fluid or paste like compositions is their transformation into near solid phase in the presence of aqueous fluid such as water, aqueous buffers or crevicular fluid. For example, when a sample of such a gel is placed into a tube containing water or human serum, the composition becomes nearly solid in the receptor phase. This is believed to be due to insolubility of the poly(lactyl-co-glycolide) copolymers in water, and related aqueous solvents. Thus, even though such fluid compositions can be used advantageously when desired from syringe like apparatus, they still offer uncompromised advantages of solid devices at the treatment sites. Further, since such polymeric materials do undergo slow degradation via hydrolysis, the drug continues to release in a sustained manner from such compositions.

For the purpose of experimental evaluation, stainless steel wire loops were fabricated to provide 0.5 cm. internal diameter. Loops were filled with test compositions, and the test samples were lowered into vials filled with pH 7.4 phosphate buffers. In contact with the fluid receptor a gel of Example V transformed into near solid phase in about a minute. Initially, the drug is released to provide a burst, during the phase transition stage providing a loading dose. Once the gel transforms into solid phase, drug release rate slows down to a more controlled rate. This dual phase release pattern is, in fact, highly desirable in practice for the treatment of microbial infection. The receptor fluids of each of the test vials were exchanged with same volume of the fluid every day for at least seven days for the purpose of this experiment.

Results of this experiment showed that the drug is released from such gel compositions in a sustained manner.

Quantity of the drug released from the respective compositions can be varied by selecting factors such as solubility of drug by proper selection of its salt or ester, drug loading in the composition, molecular weight of the copolymer or adding other polymer. The composition of the Example IV, containing tetracycline hydrochloride salt releases drug at a faster rate compared to the drug released from the composition of the Example V. This is due to the fact that the hydrochloride salt of tetracycline is about six times more soluble than the tetracycline base.

This series of experiments demonstrate that sustained release fluid gel or paste compositions of poly(lactyl-co-glycolide) can be formulated using propylene carbonate like pharmaceutically acceptable solvent of this invention without using any objectionable organic solvents such as acetone or methylene chloride for delivery of the drugs into the body cavities.

What is claimed:

1. A liquid, semi-solid or solid composition suitable for insertion into or around the periodontal pocket of a person or lower animal suffering from diseases of the oral cavity comprising a copolymer of lactide and glycolide in a concentration from about 10% to about 90% wherein the molar percentage centage of lactide units is from about 15% to about 85%, a active drug selected from the group consisting of antiinflammatory agents, antimicrobials, antibiotics, peroxides, anesthetic agents and vitamins in a concentration from about 1% to about 90% and propylene carbonate in a concentration from about 0.1% to about 90%, the ratio of the components being such that the drug active is released at a rate to provide steady state number average concentrations of from about 10 micrograms to about 2000 micrograms per milliliter of the gingival crevicular fluid of a treated periodontal pocket.

2. A composition according to claim 1 wherein the number average molecular weight of the copolymer is from about 1000 to about 120,000.

3. A composition according to claim 2 wherein the concentration of the active drug drug active is from about 10% to about 50% and the active is selected from the tetracycline group of antibiotics.

4. A composition according to claim 3 wherein the composition is formed into a semi solid or solid shape having a width of from about 0.1 mm to about 5 mm, a thickness of from about 0.01 mm to about 2 mm and a length of from about 1 mm to about 15 mm.

5. A method of treating diseases of the oral cavity in a person or lower animal suffering from such disease by placing into the periodontal pocket or around said pocket of said person or lower animal a composition according to claim 1.

6. A method according to claim 5 wherein the active drug active is selected from the tetracycline group of antibiotics.

7. A method according to claim 6 wherein the composition is formed into a shape having a semi solid or solid width of from about 0.1 mm to about 5 mm, a thickness of from about 0.01 mm to about 2 mm and a length of from about 1 mm to about 15 mm.

* * * * *